United States Patent [19]

Sapper

[11] Patent Number: 4,705,549
[45] Date of Patent: Nov. 10, 1987

[54] SEPARATION OF $C_{3+}$ HYDROCARBONS BY ABSORPTION AND RECTIFICATION

[75] Inventor: Rainer Sapper, Neuried, Fed. Rep. of Germany

[73] Assignee: Linde Aktiengesellschaft, Wiesbaden, Fed. Rep. of Germany

[21] Appl. No.: 809,953

[22] Filed: Dec. 17, 1985

[30] Foreign Application Priority Data

Dec. 17, 1984 [DE] Fed. Rep. of Germany ....... 3445961

[51] Int. Cl.$^4$ ............................................. F25J 3/02
[52] U.S. Cl. .......................................... 62/30; 62/17; 62/20; 62/24; 62/27; 62/28; 62/31; 62/38; 62/39; 208/341; 208/342; 208/343
[58] Field of Search ................... 62/17, 20, 38, 39, 28, 62/30, 31, 34, 24, 27; 208/341, 342, 343

[56] References Cited

U.S. PATENT DOCUMENTS

| | | | |
|---|---|---|---|
| 3,932,156 | 1/1976 | Stern | 62/20 |
| 4,272,269 | 6/1981 | Hammond et al. | 62/28 |
| 4,486,209 | 12/1984 | Fabbri et al. | 62/30 |
| 4,507,133 | 3/1985 | Khan et al. | 62/29 |
| 4,542,517 | 4/1986 | Burr et al. | 62/28 |
| 4,548,629 | 10/1985 | Chiu | 62/24 |
| 4,584,006 | 4/1986 | Apffel | 62/30 |
| 4,592,766 | 6/1986 | Kumman et al. | 62/31 |
| 4,596,588 | 6/1986 | Cook | 62/28 |
| 4,597,788 | 7/1986 | Apffel | 62/28 |
| 4,600,421 | 7/1986 | Kumman et al. | 62/34 |
| 4,608,068 | 8/1986 | Bauer et al. | 62/31 |
| 4,617,039 | 10/1986 | Buck | 62/30 |

Primary Examiner—Asok Pal
Attorney, Agent, or Firm—Millen & White

[57] ABSTRACT

The separation of $C_{3+}$ hydrocarbons from natural gas and the like comprises subjecting the gas under pressure to partial condensation under cooling, separating the uncondensed gaseous phase and engine expanding same while the condensed liquid fraction is subjected to rectification. Additional $C_{3+}$ hydrocarbons are separated from the engine expanded gaseous fraction by scrubbing and then fed to the rectification column. The resultant scrubbed gaseous fraction, whose pressure preferably is above the rectification pressure, can be delivered as $C_{2-}$ product stream.

22 Claims, 1 Drawing Figure

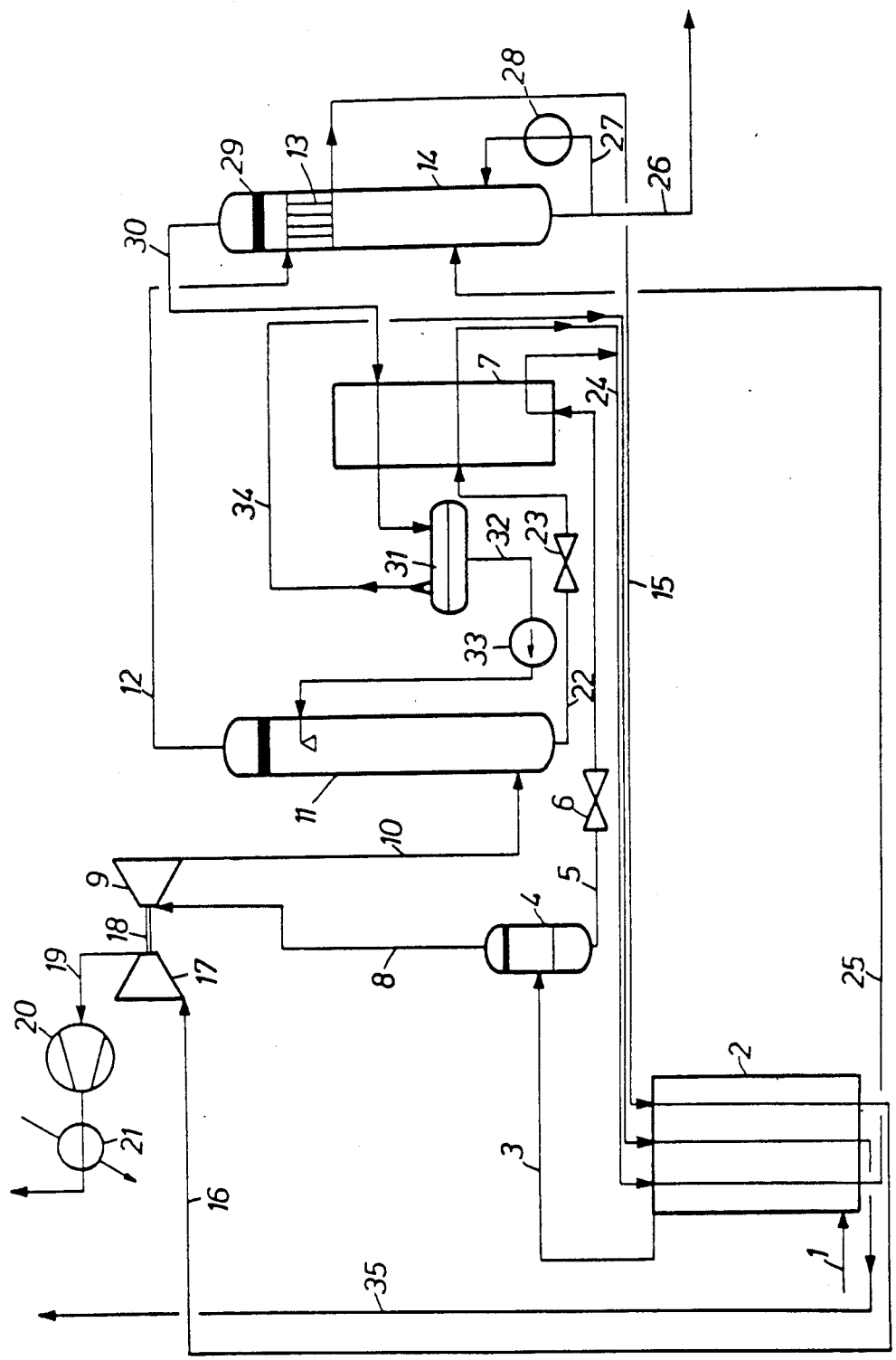

SEPARATION OF $C_{3+}$ HYDROCARBONS BY ABSORPTION AND RECTIFICATION

CROSS REFERENCE TO RELATED APPLICATION

This application is related to concurrently filed and commonly assigned applications entitled: "Process for the Separation of $C_{3+}$ Hydrocarbon from a Pressurized Hydrocarbon Stream", Bauer, Ser. No. 809,957; "Process for Separation of a $C_{2+}$, or $C_{3+}$ or $C_{4+}$ Hydrocarbons" Bauer, Ser. No. 809,956; and "Process for Separation of $C_{2+}$ or $C_{3+}$ Hydrocarbons", Bauer Ser. No. 809,958, all incorporated by reference herein.

BACKGROUND OF THE INVENTION

This invention relates to a process for the separation of $C_{3+}$ hydrocarbons from a gas stream under superatmospheric pressure, said gas stream being cooled, partially condensed and separated into a liquid and a gaseous fraction and wherein the gaseous fraction, is engine expanded (expansion while performing external work—also called work expansion) and the liquid fraction is fractionated by rectification into a product stream containing mostly $C_{3+}$ hydrocarbons and a residual gas stream containing mostly lower boiling components.

Such processes are used, for example, in obtaining an LPG fraction ($C_3/C_4$ hydrocarbons) from natural gases or refinery gases, or in separating propane and higher hydrocarbons (optionally unsaturated hydrocarbons as well) from refinery or cracked gases. A process of this kind is described in an earlier German patent application No. P 34 08 760.5 filed Mar. 9, 1984 in Germany having a common assignee and corresponding substantially to U.S. application Ser. No. 709,742 filed Mar. 8, 1985 by Bauer et al, said U.S. application being incorporated by reference herein. An important feature of this earlier application is that the cold obtained during engine expansion of the gaseous fraction remaining after partial condensation is used not for production of reflux liquid in the rectification column, but instead for the cooling and partial condensation of the crude gas. Therefore, in this process it is unnecessary to feed the light components of the gas stream into the rectification column. The elimination of the introduction of the light components of the feedstock stream (especially $C_1$ and $C_2$ hydrocarbons) into the column makes it possible to perform the rectification at a higher temperature. Thus, the possibility of using a simple and inexpensive external cold cycle for cooling the overhead from the rectification column constitutes a considerable improvement in conducting the process. Nevertheless a further improvement is still desirable, especially to increase the yield of separated $C_{3+}$ hydrocarbons without having to pass entire feed stream into the rectification column, or without having to perform the partial condensation at a lower temperature. In the process of the above described application, a particular disadvantage is the substantial compressor power required for recompression of the light fractions in those cases where the $C_{2-}$ fraction is to be delivered under high pressure (e.g., into a natural gas pipeline).

SUMMARY

An object of one aspect of this invention is to provide a system of the type described above, facilitating separation of the $C_{3+}$ hydrocarbons.

Upon further study of the specification and appended claims, further objects and advantages of this invention will become apparent to those skilled in the art.

To achieve these objects, additional $C_{3+}$ hydrocarbons are separated from the engine expanded gaseous fraction by a scrubbing step. The loaded scrubbing agent is preferably fed to the rectification column, while the unabsorbed gaseous fraction coming from the scrubbing step is preferably heated and delivered as a product stream containing $C_{2-}$ hydrocarbons.

Whereas in the older process, the engine expanded gaseous fraction is heated in next step against the gas streams that are to be cooled and then delivered as product gas, according to the present invention, the heavy components still contained in the engine expanded gas are separated by a scrubbing step and preferably fed to the rectification column to obtain a higher yield of then $C_{3+}$ hydrocarbon cut.

In a preferred embodiment of the invention, scrubbing is conducted at a higher pressure than rectification, i.e., the work expansion conducted to a pressure substantially higher than is the rectification pressure. For example, the scrubbing pressure is preferably about 10 to 20 bar higher than the rectification pressure. This proves to be especially advantageous if the $C_{2-}$ fraction is to be delivered under high pressure after it has been heated, since less energy-intensive recompression is required, or under the most advantageous conditions can even be completely eliminated.

The scrubbing step is preferably performed with a liquid hydrocarbon mixture derived from the process itself, although other scrubbing agents, particularly other liquid hydrocarbon mixtures, are suitable for this purpose. In a particularly preferred embodiment of the invention, the scrubbbing is conducted with a scrubbing agent obtained by partial condensation of the residual gas from the rectification column. The partial condensation of the residual gas can be produced in this case by heat exchange with any process stream or coolant having a lower temperature than that of the head of the rectification column. In this connection, it is preferable to condense only about enough scrubbing agent for attaining the desired $C_{3+}$ yield. Use of the residual gas as scrubbing agent is particularly advantageous, since the $C_{3+}$ hydrocarbons still contained in the residual gas selectively condense during partial condensation and, after the scrubbing step, are preferably passed to the rectification column, and in this way, are not completely lost with the residual gas.

In another preferred embodiment of the invention, the partial condensation of the residual gas is conducted by heat exchange with the evaporating bottoms product from the scrubbing step. In a particularly advantageous further development of this embodiment of the process, the pressures in the scrubbing step and in the rectifiction step are so coordinated that the residual gas, without the need for compression, partially condenses in indirect heat exchange with said evaporating bottoms product. This step of the process, therefore, occurs at about the pressure of rectification. Furthermore, it is advantageous to subject the partially condensed residual gas to a phase separation step and to pump only the liquid phase into the scrubbing column at the required pressure, this being especially energy efficient and expeditions. The uncondensed portion of the residual gas, after being heated against the process stream that is to be cooled, can be delivered as a separate product stream, for example as fuel gas, at about rectification pressure (reduced by the unavoidable pipeline and apparatus pressure losses).

The $C_{2-}$ fraction unabsorbed in the scrubbing step constitutes an excellent low temperature source, and in an advantageous further embodiment of the invention is employed for cooling the head of the rectification column and thereafter is passed into heat indirect exchange with the feed gas stream that is to be cooled.

It is preferred that both the liquid phase collecting after partial condensation of the feed gas, and the bottoms product from the scrubbing step are fed into the rectification column. In this case, it is advantageous to perform a partial evaporation of these fractions before rectification, which, e.g., can be done by heat exchange with the condensing residual gas from the rectification and/or with the gas stream that is to be cooled. The two liquid fractions can be fed separately into the rectification column, in which case each of the feeds, depending on the composition of the liquid fractions, is passed into the column at a plate having a similar composition. But often, especially in the case of compositions of liquid fractions that differ only slightly from one another, it is advantageous to mix these fractions after expansion to achieve a common pressure level. It is also preferred to heat the resultant mixture at least partially before it is introduced into the rectification column, and especially in indirect heat exchange relationship with the incoming gaseous feed.

The process according to the invention is particularly suitable for treating a relatively light gas stream, i.e., a stream that contains a high proportion of $C_1$ and $C_2$ hydrocarbons, especially if the $C_1/C_2$ product gas is to be delivered under high pressure. A light gas is to be generally understood as a gas, especially a natural or refinery gas whose methane plus ethane component is over 90% by mols, but having a $C_{3+}$ fraction of at least about 1%, preferably at least 2% by mols,. In processing such a gas, both the scrubbing and the rectification steps are operated at the highest possible pressure. The high pressure in the scrubbing stage is preferable because the main amount of marketable gas that is to be delivered into a natural gas pipeline is separated therein. The high pressure in the scrubbing stage thus permits a substantial reduction in the required power for recompression. The high pressure in the rectification step is preferable since the residual gas obtained as overhead, for the most part is to be liquefied to form scrubbing agent, and liquefaction is preferably to be done without prior compression of the residual gas. In general the pressures for the scrubbing stage are between 35 and 45 bar, e.g., at 43 bar, and for the rectification between 25 and 32 bar, e.g., at 30 bar.

The process is suitable for processing a light natural gas particularly if, as the $C_{3+}$ fraction to be separated, a liquid gas desired which exhibits commercial LPG quality and consists of approximately 30% propane and 70% butane. In such an embodiment a very high degree of separation of $C_{4+}$ hydrocarbons is desired, while the $C_{3+}$ yield is relatively small and, for example, constitutes about 20 to 60% of the propane contained in the gas stream. This means that in this special case, 40%–80% of the propane is passed into the overhead residual gas.

In any case, this invention is advantageous when applied to any gas stream containing preferably about 80 to 99 mol percent of $C_{2-}$ hydrocarbons and about 1 to 20 mol percent of $C_{3+}$ hydrocarbons.

BRIEF DESCRIPTION OF THE DRAWINGS

Various other objects, features and attendant advantages of the present invention will become more fully appreciated as the same becomes better understood when considered in conjunction with the accompanying drawing, wherein the figure is a preferred comprehensive embodiment of the invention.

Detailed Description of Drawing

In the embodiment represented in the figure, a natural gas, which contains 92.6% methane (indications of percentage in each case are in mol %), 4.3% ethane, 1.3% propane, 0.55% butane and 0.25% $C_{5+}$ hydrocarbons as well as 1.0% of inerts (nitrogen and carbon dioxide), at a pressure of 69 bar and a temperature of 315 K. is fed by a pipe 1 and cooled to 234 K. in a heat exchanger 2 against process streams that are heated. The natural gas, partially condensed during cooling, is withdrawn via pipe 3 and subjected to separation in phase separator 4. The condensate, withdrawn via pipe 5, contains 1.2% $CO_2$, 54.0% methane, 11.5% ethane, 9.6% propane, 9.8% butane and 13.9% $C_{5+}$ hydrocarbons. It is expanded in valve 6 to a pressure of about 30 bar and, after partial heating in heat exchanger 7, is mixed with a process stream described below. A gaseous fraction is removed from phase separator 4 by pipe 8 and expanded in expansion turbine 9 to a pressure of 43 bar, whereby the gas is cooled to 211 K. In this expansion, the greater part of the $C_{3+}$ hydrocarbons still contained in the gas condenses in the liquid phase of the two-phase exit stream, which contributes to the $C_{3+}$ yield in the process. This two-phase mixture is introduced into the lower part of a scrubbing column 11, in which it is acted on by a scrubbing liquid also described below. After the separation of additional $C_{3+}$ components by scrubbing, there is removed at the head of the scrubbing column by pipe 12 a light gas, which, after being heated from 210 K. to 214 K. in heat exchanger 13 of rectification column 14, is withdrawn via pipe 15 and heated to 302 K. in heat exchanger 2 against natural gas to be cooled. Thereafter, the residual gas is fed by pipe 16 to a compressor 17, which is driven by a shaft 18 of expansion turbine 9. The residual gas is then passed via pipe 19 into a compressor 20, in which the gas is compressed to a delivery pressure of 72 bar. After the heat of compression is removed in heat exchanger 21, the residual gas is delivered at a temperature of 315 K.

A liquid, at a temperature of 211 K., which contains 1.6% carbon dioxide, 57.5% methane, 16.9% ethane, 14.5% propane, 8.8% butane and 0.7% $C_{5+}$ hydrocarbons, is withdrawn via conduit 22 from the bottom of scrubbing column 11. This liquid is expanded in valve 23 to a pressure of about 30 bar, heated in heat exchanger 7, then mixed with the condensate from phase separator 4 after the condensate is likewise heated in heat exchanger 7. The resultant mixture is then fed by pipe 24 into heat exchanger 2, where further heating occurs against natural gas being cooled and partially condensed. At a temperature of 302 K., the resultant mixture, is introduced by pipe 25 into rectification column 14, wherein the $C_{3+}$ hydrocarbons are separated from the lighter components. A $C_{3+}$ product fraction, which contains 1.3% ethane, 28% propane, 49.1% butane and 21.6% $C_{5+}$ hydrocarbons is removed from the bottom of the column by pipe 26. A part of the bottoms product from the rectification column is branched off by pipe 27, heated in heat exchanger 28 and returned as reboiler heat to the lower section of column 14.

Via pipe 30, an overhead product, containing 1.9% carbon dioxide and nitrogen, 68.1% methane, 19.5% ethane and 10.5% propane and contaminated with only 100 ppm of $C_{4+}$ hydrocarbons, collects at a temperature of 261 K. in the head of the rectification column above entrainment separator 29. This gas is partially condensed without intermediate compression in heat exchanger 7 in indirect heat exchange against both (a) the bottoms product from scrubbing column 11 after said bottoms product (the loaded scrubbing agent) has been expanded to the rectification pressure and (b) the condensate from phase separator 4 after said condensate has been expanded via valve 6 to the rectification pressure. The resultant condensate is then fed into a phase separator 31, wherein a separation is performed. The resultant liquid phase 1 is removed by pipe 32 and is pressurized by pump 33 to the pressure of the scrubbing column of 43 bar, and then fed to scrubbing column 11 in the upper section thereof. The uncondensed gas collecting in separator 31 is removed by pipe 34 and, after being heated in heat exchanger 2 against natural gas that is to be cooled, the uncondensed gas is delivered by pipe 35 as residual gas at a pressure of 30 bar and a temperature of 302 K., which, can be used e.g., as fuel gas. It contains 1.3% nitrogen and carbon dioxide, 92.8% methane, 5.4% ethane and 0.5% propane.

The $C_{3+}$ product, which collects at a temperature of 396 K. and is removed by pipe 26, contains 99.4% of the $C_{4+}$ hydrocarbons contained in the gas introduced by pipe 1, while the propane yield is about 25%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a process for separation of $C_{3+}$ hydrocarbons from a feed gas stream containing essentially light hydrocarbons, wherein the feed gas stream, being under superatmospheric pressure, is cooled, partially condensed and separated into a liquid and a gaseous fraction and wherein the gaseous fraction is engine expanded and the liquid fraction is fractionated in a rectification column into a product stream containing mostly $C_{3+}$ hydrocarbons and a residual gas stream containing mostly lower boiling components, the improvement comprising scrubbing the engine expanded gaseous fraction with a scrubbing agent to absorb additional $C_{3+}$ hydrocarbons, said scrubbing agent obtained by partial condensation of said residual gas stream from the rectification column, and said scrubbing being conducted at a pressure substantially higher than that of the rectification step.

2. A process according to claim 1 further comprising passing resultant loaded scrubbing agent into the rectification column, thereby increasing the quantity of $C_{3+}$ bottoms product.

3. A process according to claim 1 further comprising heating unabsorbed gas from the scrubbing step in indirect heat exchange with the feed gas stream.

4. A process according to claim 1 further comprising recovering unabsorbed gas containing $C_2$-hydrocarbons from the scrubbing step.

5. A process according to claim 3 wherein the unabsorbed reheated gas consists essentially of $C_2$-hydrocarbons.

6. A process according to claim 2 further comprising heating unabsorbed gas from the scrubbing step in indirect heat exchange with the feed gas stream.

7. A process according to claim 6 further comprising recovering unabsorbed gas containing $C_2$-hydrocarbons from the scrubbing step.

8. A process according to claim 7 wherein the unabsorbed reheated gas consists essentially of $C_2$-hydrocarbons.

9. A process according to claim 1, wherein the partial condensation of the residual gas is conducted by heat exchange with loaded scrubbing agent from the scrubbing step.

10. A process according to claim 1, wherein the partial condensation of the residual gas takes place at the rectification pressure.

11. A process according to claim 1, wherein the partially condensed residual gas is subjected to a phase separation step and the liquid fraction is used as the scrubbing agent.

12. A process according to claim 9, wherein the partially condensed residual gas is subjected to a phase separation step and the liquid fraction is used as the scrubbing agent.

13. A process according to claim 11, wherein the liquid fraction is pumped to the pressure of the scrubbing step.

14. A process according to claim 12, wherein the liquid fraction is pumped to the pressure of the scrubbing step.

15. A process according to claim 1, wherein the gaseous fraction from the scrubbing step is passed into the head of the rectification column and by indirect heat exchange cools the head of the column.

16. A process according to claim 1, wherein the gaseous fraction from the scrubbing step is passed into the head of the rectification column and by indirect heat exchange cools the head of the column.

17. A process according to claim 11, wherein the liquid fraction separated after partial condensation of the gas stream, is mixed with the loaded scrubbing agent from the scrubbing step and the resultant mixture is heated and then introduced into the rectification column.

18. A process according to claim 1, wherein the liquid fraction separated after partial condensation of the gas stream, is mixed with the loaded scrubbing agent from the scrubbing step and the resultant mixture is heated and then introduced into the rectification column.

19. A process according to claim 1, further comprising expanding resultant loaded scrubbing agent from the scrubbing step and then passing resultant expanded loaded scrubbing agent into the rectification column.

20. A process according to claim 19, wherein said resultant expanded loaded scrubbing agent is heated by indirect heat exchange with said residual gas stream prior to delivery of said resultant expanded loading scrubbing agent into the rectification column.

21. A process according to claim 1, wherein the scrubbing step is conducted at a pressure of about 10-20 bar higher than the pressure of the rectification step.

22. A process according to claim 11, wherein the scrubbing step is conducted at a pressure of about 10-20 bar higher than the pressure of the rectification step.

* * * * *